United States Patent
Barias et al.

(10) Patent No.: US 11,999,672 B2
(45) Date of Patent: Jun. 4, 2024

(54) HIGH PURITY ISOAMYLENE PRODUCTION FROM TERTIARY AMYL METHYL ETHER DECOMPOSITION

(71) Applicant: LUMMUS TECHNOLOGY LLC, Houston, TX (US)

(72) Inventors: Rosette Barias, Houston, TX (US); Liang Chen, Houston, TX (US); Michael Jon Scott, Houston, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 112 days.

(21) Appl. No.: 17/930,905

(22) Filed: Sep. 9, 2022

(65) Prior Publication Data

US 2023/0002294 A1    Jan. 5, 2023

Related U.S. Application Data

(62) Division of application No. 17/453,241, filed on Nov. 2, 2021, now Pat. No. 11,465,949.

(60) Provisional application No. 63/108,665, filed on Nov. 2, 2020.

(51) Int. Cl.
- *C07C 1/20* (2006.01)
- *C07C 7/04* (2006.01)
- *C07C 7/10* (2006.01)

(52) U.S. Cl.
CPC .................. *C07C 1/20* (2013.01); *C07C 7/04* (2013.01); *C07C 7/10* (2013.01)

(58) Field of Classification Search
CPC ................ C07C 1/20; C07C 7/04; C07C 7/10
See application file for complete search history.

(56) References Cited

U.S. PATENT DOCUMENTS 7,410,555 B2 *   8/2008   Groten ..................... C07C 2/06
                                                                          203/29

* cited by examiner

*Primary Examiner* — Thuan D Dang
(74) *Attorney, Agent, or Firm* — Osha Bergman Watanabe & Burton LLP

(57) ABSTRACT

Systems and methods for the production of a high purity isoamylene product. The isoamylene in a mixed hydrocarbon stream may initially be converted to TAME via etherification, and a subsequent decomposition of the TAME may result in a high purity isoamylene stream with very low impurities that is suitable for a variety of petrochemical applications, such as for use in the production of fragrances, pesticides, peroxides, polymer antioxidants, UV stabilizers and hydrocarbon resins.

17 Claims, 2 Drawing Sheets

HIGH PURITY ISOAMYLENE PRODUCTION FROM TERTIARY AMYL METHYL ETHER DECOMPOSITION

FIELD OF THE DISCLOSURE

Embodiments of the present disclosure generally relate to production of isoamylene. More specifically, embodiments herein relate to production of a high purity isoamylene product via decomposition of tertiary methyl amyl ether.

BACKGROUND

Tertiary Amyl Methyl Ether (TAME) is often used as a gasoline blending component to increase the oxygen content of the fuel. Future gasoline specifications, such as the Euro VI/BS VI gasoline specifications, may result in decreased usage of blending pool TAME products.

Isoamylene, on the other hand, is used as a raw material for fragrances, pesticides, peroxides, polymer antioxidant, UV stabilizers and hydrocarbon resin. Unfortunately, isoamylene present in mixed hydrocarbon streams at a refinery, such as in a steam cracker C5 cut or a light naphtha cut, is difficult to separate from linear pentenes, and thus difficult to obtain in a high purity product stream through conventional distillation.

SUMMARY OF THE CLAIMED EMBODIMENTS

Embodiments herein are directed toward systems and methods for the production of a high purity isoamylene product. The isoamylene in a mixed hydrocarbon stream may initially be converted to TAME via etherification, and a subsequent decomposition of the TAME may result in a high purity isoamylene stream with very low impurities that is suitable for a variety of petrochemical applications, such as for use in the production of fragrances, pesticides, peroxides, polymer antioxidants, UV stabilizers and hydrocarbon resins.

In one aspect, embodiments herein relate to a process for producing a high purity isoamylene stream. The process includes purifying a crude tertiary amyl ether stream, comprising tertiary amyl ether, tertiary amyl alcohol, diisoamylene, C5 hydrocarbons including linear pentenes and pentanes, alcohol, and water, to recover a lights stream comprising the C5 hydrocarbons and tertiary amyl alcohol, a heavies stream comprising diisoamylene, and a tertiary amyl ether containing stream. The process further includes feeding the tertiary amyl ether containing stream as a vapor to a decomposition reactor containing a decomposition catalyst, and contacting the tertiary amyl ether with the decomposition catalyst to convert the tertiary amyl ether to isoamylene and alcohol and to recover an isoamylene containing rector effluent. The isoamylene containing reactor effluent is then fed to a separation zone and separated into an alcohol stream, a vent stream, an isoamylene product stream, and a heavy oxygenate stream comprising unreacted ethers and tertiary amyl alcohol. Optionally, the process may further include feeding the heavy oxygenate stream to the purifying step.

In some embodiments, the contacting in the decomposition reactor occurs at a reaction temperature in a range from about 130° C. to about 260° C. and at a pressure in a range from about 2 barg to about 12 barg.

In some embodiments, the process further includes forming the crude tertiary amyl ether feedstock, which may include: feeding a C1-C2 alcohol and a mixed C5 stream to a fixed bed reactor containing an etherification catalyst, contacting the C1-C2 alcohol and isoamylene with the etherification catalyst to convert a portion of the isoamylene and C1-C2 alcohol to tertiary amyl ether, and recovering a fixed bed reactor effluent; feeding the fixed bed reactor effluent to a catalytic distillation reactor for concurrently (i) reacting isoamylene with the C1-C2 alcohol to produce additional tertiary amyl ether and (ii) recovering a bottoms stream comprising the tertiary amyl ether and an overhead stream comprising unreacted C5s and unreacted C1-C2 alcohol; and feeding the bottoms stream as the crude tertiary amyl ether stream to the purifying step.

In some embodiments, the alcohol comprises methanol, the tertiary amyl ether comprises tertiary amyl methyl ether, and wherein the alcohol stream comprises at least 99.8 wt % methanol. In other embodiments, the alcohol comprises ethanol, and the tertiary amyl ether comprises tertiary amyl ethyl ether.

In another aspect, embodiments herein relate to a system for producing a high purity isoamylene stream. The system may include a purification zone comprising a divided wall distillation column configured to receive a crude tertiary amyl ether from a feed source, the divided wall distillation column configured to separate the crude tertiary amyl ether into an overhead lights stream, a bottom heavies stream, and a tertiary amyl ether containing side draw stream. A heat exchanger is provided for vaporizing the tertiary amyl ether containing side draw stream, which is fed to a decomposition reactor containing a decomposition catalyst configured to convert the tertiary amyl ether into isoamylene and alcohol and to produce a reaction effluent. A separation zone is also included in the system, configured to receive the reaction effluent and to separate the reaction effluent into an alcohol stream, a vent stream, a heavy oxygenate stream, and an isoamylene product stream.

In some embodiments, the system may include a feed line for feeding the heavy oxygenate stream to the purification zone.

In some embodiments, the system may further include a reaction zone configured to react an isoamylene containing stream with methanol to produce the crude tertiary amyl ether. In such embodiments, the separation zone may include: an isoamylene lights column configured to receive the reactor effluent and to separate the reactor effluent into an overhead stream and a bottoms stream comprising the heavy oxygenates, recovered as the heavy oxygenate stream; a methanol extraction column, configured to receive the overhead stream from the isoamylene lights column and to recover an overheads stream and to recover the alcohol stream as a bottoms stream; and an isoamylene finishing column, configured to receive the overheads stream from the methanol extraction column and to recover the vent stream as an overheads product and to recover the isoamylene product stream as a bottoms product. The system may also include a flow line for feeding the alcohol stream to the reaction zone.

In other embodiments, the separation zone comprises: a methanol extraction column, configured to receive the reactor effluent and to separate the reactor effluent into an overhead stream and a bottoms stream comprising the alcohol, recovered as the alcohol stream; an isoamylene lights column configured to receive the overhead stream from the methanol extraction column and to recover the vent stream as an overheads and a bottoms stream; and a heavies column, configured to receive the bottoms stream from the isoamylene lights column and to recover the isoamylene product stream as an overheads product and to recover the heavy oxygenate stream as a bottoms product. Some embodiments may include a methanol finishing column configured for receiving the alcohol stream and for producing a purified alcohol product stream.

Other aspects and advantages will be apparent from the following description and the appended claims.

DETAILED DESCRIPTION

Figure 1:
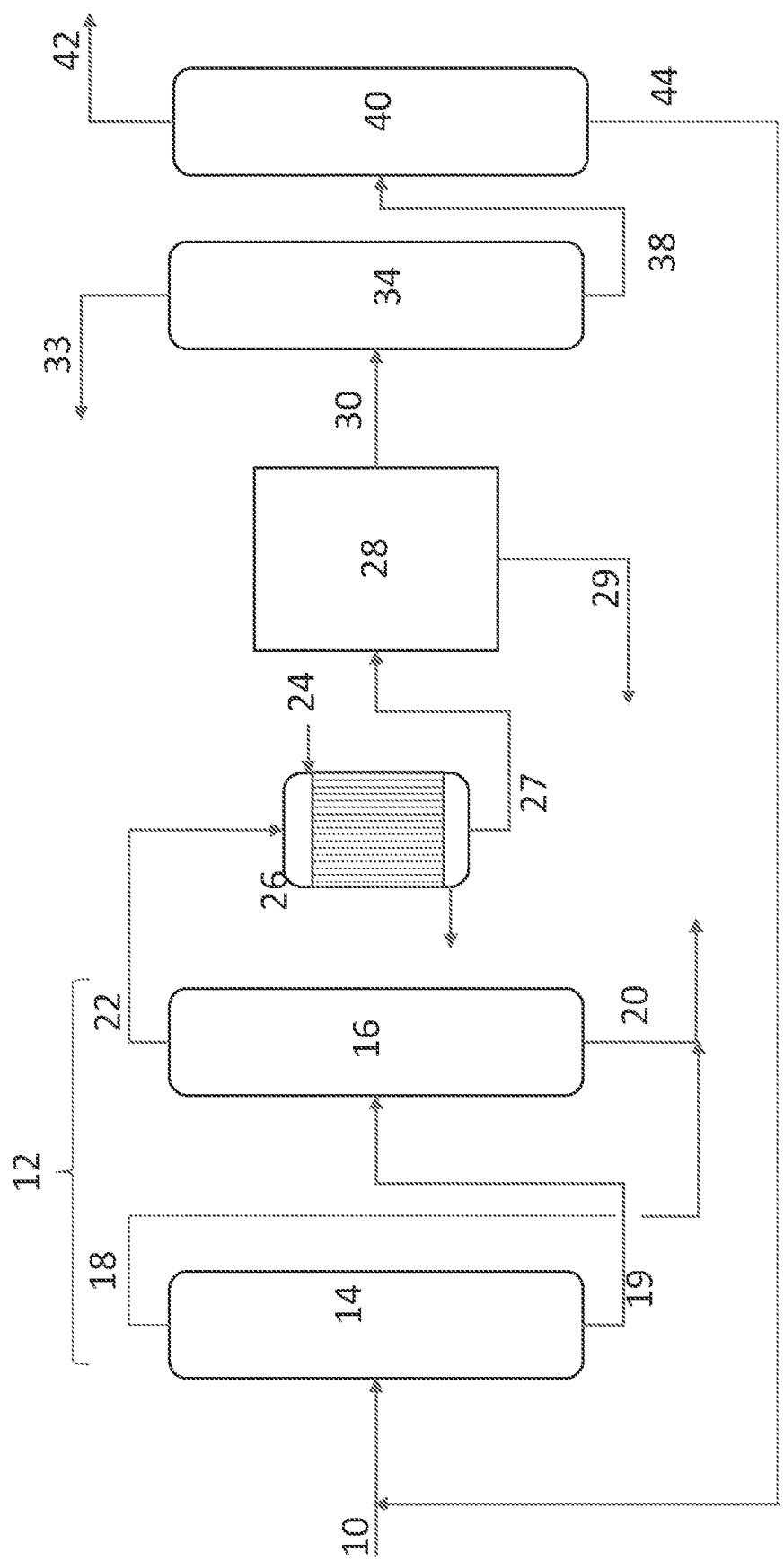
FIG. 1 illustrates a simplified process flow diagram for producing a high purity isoamylene according to one or more embodiments disclosed herein.

Embodiments of the present disclosure generally relate to production of isoamylene. More specifically, embodiments herein relate to production of a high purity isoamylene product via decomposition of tertiary amyl alkyl ether. Even more specifically, embodiments herein relate to production of a high purity isoamylene product via decomposition of tertiary amyl methyl ether (TAME).

ISOAMYL ETHER PRODUCTION

TAME and other isoamyl ethers may be produced by reaction of isoamylene with an alcohol. The reaction of an alcohol and an olefin and separation of the reactants from the reaction products by fractional distillation has been practiced for some time. The process is variously described in U.S. Pat. Nos. 4,232,177; 4,307,254; 4,336,407; 4,504,687; 4,987,807; 4,950,803; and 5,118,873. Other more recent patents discussing the production of TAME or co-production of TAME and MTBE include U.S. Pat. Nos. 6,232,509; 5,248,837; 6,232,509, 5,792,891; 7,553,995; 6,583,325; 7,141,705; 7,030,277; and 9,254,479, among others.

Various feed streams containing isoamylene in admixture with other hydrocarbons may be used to produce isoamyl ethers. Feed streams and sources suitable for the production of TAME or other isoamyl ethers include hydrocarbon fractions including C5 hydrocarbons that contain isoamylenes, specifically 2-methyl-1-butene and 2-methyl-2-butene. Refinery streams are usually separated by fractional distillation, and a light naphtha cut is one such refinery stream. Because they often contain compounds that are very close in boiling points, such refinery separations are not precise. A refinery C5 stream, for instance, may contain C4s and up to C8s and higher. Hydrocarbon components in these mixtures may be saturated (alkanes), unsaturated (mono-olefins), or poly-unsaturated (diolefins). Additionally, the components may be any or all of the various isomers of the individual compounds. Such refinery mixtures can easily contain 150 to 200 components, including the desired isoamylenes. In addition to a light naphtha cut, other isoamylene-containing hydrocarbon streams may be utilized in the present process, including a C4-C5 cut, a C5 cut, a C4-C6 cut, a C5-C6 cut, and many other C5-containing mixtures as may be envisioned by one skilled in the art. In some embodiments herein, TAME production is from a feed source with minor amounts of C4s and majority of the cut is C5s; some small percentage may be C6s but for gasoline blending, lifting of the C6s in the depentanizer is limited to avoid having a bigger TAME unit.

As an example of the production of TAME, methanol and the isoamylene containing C5 stream may be fed to a reactor or a catalytic distillation column where they are contacted with a catalyst. The methanol preferentially reacts with isoamylene, forming TAME. When produced in a catalytic distillation column, the TAME is typically heavier than the unreacted C5 components of the feed mixture and the methanol, hence it drops in the column and may be collected as a bottoms fraction. Concurrently, the unreacted C5's (e.g. n-pentane, n-pentenes) are lighter and may be collected as an overhead fraction. Similar reactions may occur between ethanol and isoamylene, forming tertiary amyl ethyl ether (TAEE). The ethers product usually has 1-2 wt % of unreacted C5s to maximize the TAME product purity.

TAME and other isoamyl ethers may be formed by the reaction of isoamylene and methanol (alcohol) at mild operating conditions over an acid catalyst. The selectivity of this reaction is limited by equilibrium constraints. By using a catalytic distillation column, essentially complete conversion is attainable. The alcohol and isoolefin are fed to a distillation column reactor having a distillation reaction zone containing a suitable catalyst, such as an acid cation exchange resin, in the form of catalytic distillation structure. As embodied in the etherification of isoamylene, the olefin and an excess of methanol may be first fed to a fixed bed reactor wherein most of the olefin is reacted to form the corresponding ether, tertiary amyl methyl ether (TAME). The fixed bed reactor may be operated at a given pressure such that the reaction mixture is at the boiling point, thereby removing the exothermic heat of reaction by vaporization of the mixture.

The effluent from the fixed bed reactor is then fed to the distillation column reactor wherein the remainder of the isoamylenes are converted to the ether and the methanol is separated from the ether, which is withdrawn as bottoms. The C5 olefin stream generally contains only about 10 to 60 percent olefin, the remainder being inerts that are removed in the overheads from the distillation column reactor. The overhead hydrocarbon raffinate contains an amount of methanol up to the azeotropic concentration of about 12 wt %. This stream may then be washed with water to separate methanol from the hydrocarbons. Methanol is then distilled to remove the water.

The etherification processes typically utilizes strongly acidic ion exchange resins as etherification catalysts, which are strongly acidic organic polymers. As an isoamylene molecule meets alcohol at an active site, the reaction takes place rapidly forming ether.

The bottoms product, as noted above, contains the isoamyl ether, such as TAME. In addition to the isoamyl ether, the bottoms product, being a crude or commercial grade isoamyl ether product, may contain various C5s, C6s, C7+components. Depending upon the efficiency of the upstream etherification process and the separations therein, the resulting commercial grade isoamyl ether, such as TAME, may include C5s, C6s, C7+, methanol, water, diisoamylene (DIA) and tertiary amyl alcohol (TAA), among other components, byproducts, and impurities.

HIGH PURITY ISOAMYLENE PRODUCTION

The crude or commercial grade isoamyl ether, which may be produced as described above, for example, may then undergo feed separations, back-cracking, and product separations to recover a high purity isoamylene product. Catalysts that may be used to facilitate the cracking of the ethers to form olefins and alcohols may include various acidic catalysts, including acid-treated silica-alumina catalysts, zeolites, and HF treated clays, among others known in the art.

In some embodiments, commercial grade TAME containing C5s, C6s, C7+, methanol, water, diisoamylene (DIA) and tertiary amyl alcohol (TAA) first undergoes removal of the C5s, C6s, C7+, DIA, methanol and some TAA in the feed purification section. The feed purification section is composed of a Lights and a Heavies Column in tandem. The Lights Column removes the bulk of the C5s, C6s, Methanol. The Heavies Column removes the DIA, some TAA and majority of the C7+. The purified TAME is superheated and vaporized via high pressure steam then fed into a decomposition reactor wherein the decomposition reactions take place. As the TAME decomposition is an endothermic reaction, either medium or high pressure steam is used to provide the heat needed in the decomposition reactors. The vapor phase decomposition reaction is carried out between 130° C. to 260° C. at a pressure of 2 to 12 barg. TAME then decomposes to 2-methyl 1-butene and 2-methyl 2-butene (referred to as isoamylenes or IA). Any remaining TAA present in the reactor feed also decomposes to isoamylenes and water, at the same decomposition rate. The methanol produced from the decomposition reaction also forms DME as a by-product. Other by-products formed in the reactor are DIA, isopentane and linear pentenes. As the TAME decomposition reactions can be carried out in lower conditions, there is lesser formation of DME and DIA as compared to MTBE decomposition. The reactor effluent is then washed in a methanol extraction column via countercurrent water washing to recover the methanol. The overhead of the methanol extraction column comprised of IA, linear pentenes, DME, DIA, and unconverted TAME is then sent to a Crude Column to separate the C5s and DME in the overhead and the unconverted oxygenates and DIA in the bottoms. The placement of the Methanol Extraction Column and Crude Column in the TAME decomposition unit typically depends on whether the decomposition unit is integrated with the upstream TAME unit or just standalone. The bottoms of the Crude column can either be recycled to the front end feed purification section to remove the DIA formed and to optimize the production of IA from the unconverted TAME or sent to the upstream TAME unit. The bottoms of the Methanol Extraction Column comprised mainly of methanol, water and some TAA are then sent to a Methanol Recovery Column (MRC) to recover methanol. Depending on the amount of TAA present in the MRC feed, a side draw is taken from the tower to purge out any TAA. The overhead of the Crude Column composed mostly of the C5s and DME is then sent to an Isoamylene Purification Tower where DME is vented. The bottoms is the high purity isoamylene. The methanol recovered from the MRC is then sent to the upstream TAME unit to reduce the methanol requirement of the TAME unit or to an optional Methanol Finishing Column to further purify the methanol and produce commercial grade methanol with purity of 99.90 wt % as a minimum In other embodiments, commercial grade TAME containing C5s, C6s, C7+, methanol, water, diisoamylene (DIA) and tertiary amyl alcohol (TAA) first undergoes removal of the C5s, C6s, C7+, DIA, methanol and some TAA in the feed purification section. The feed purification section is composed of a Divided Wall Column(DWC), combining the functions of separate Lights and Heavies Column. The DWC removes the bulk of the C5s, C6s, Methanol and TAA from the distillate of the column, while DIA, some TAA and majority of the C7+ are removed from the bottoms. The purified TAME is drawn from the side of the DWC, superheated and vaporized via high pressure steam then fed into a decomposition reactor wherein the decomposition reactions take place. Since the TAME decomposition is an endothermic reaction, high pressure steam is used to provide the heat needed in the decomposition reactors. The vapor phase decomposition reaction is carried out between 130° C. to 260° C. at a pressure of 2 to 12 barg. In various embodiments, the decomposition reaction may be carried out at a temperature in a range from a lower limit of 130° C., 135° C., 140° C., 150° C., 160° C., 170° C., 185° C., or 200° C. to an upper limit of 190° C., 200° C., 210° C., 220° C., 230° C., 240° C., 250° C., or 260° C., and at pressures in a range from a lower limit of 2, 2.5, 3, 3.5, 4, 5 or 6 barg to an upper limit of 5, 6, 7, 8, 9, 10, 11, or 12 barg. TAME then decomposes to 2-methyl-1-butene and 2-methyl-2-butene (IA). Any remaining TAA present in the reactor feed also decomposes to isoamylenes and water, at a lower decomposition rate. The methanol produced from the decomposition reaction also forms DME as a by-product. Other by-products formed in the reactor are DIA, isopentane and linear pentenes. The reactor effluent is then washed in a methanol extraction column via countercurrent water washing to recover the methanol. The overhead of the methanol extraction column comprised of IA, linear pentenes, DME, DIA, and unconverted (TAME) is then sent to a Crude Column to separate the C5s and DME in the overhead and the unconverted oxygenates and DIA in the bottoms. The bottoms of the Crude column is then recycled to the front end feed purification section to remove the DIA formed and to optimize the production of IA from the unconverted TAME. The bottoms of the Methanol Extraction Column comprised mainly of methanol, water and some TAA are then sent to a Methanol Recovery Column (MRC) to recover methanol. Depending on the amount of TAA present in the MRC feed, a side draw is taken from the tower to purge out any TAA. The overhead of the Crude Column composed mostly of the C5s and DME is then sent to an Isoamylene Purification Tower where DME is vented. The bottoms is the high purity isoamylene. The methanol recovered from the MRC is then sent to the upstream TAME unit to reduce the methanol requirement of the TAME unit or to an optional Methanol Finishing Column to further purify the methanol and produce commercial grade methanol with purity of 99.90 wt % as a minimum.

Referring now to FIG. 1, a simplified process flow diagram of a system for producing high purity isoamylene according to embodiments herein is illustrated. A commercial grade TAME stream 10 may contain C5s, C6s, C7+, methanol, water, diisoamylene (DIA) and tertiary amyl alcohol (TAA). The commercial grade TAME stream may be fed to a feed purification section 12, which may include a lights column 14 and a heavies column 16. The lights column 14 removes the bulk of the C5s, C6s, Methanol and TAA, recovered as an overheads fraction 18 from heavier components including the TAME, recovered as a bottoms fraction 19. The heavies column 16 removes the DIA, some TAA and a majority of the C7+ hydrocarbons, recovered in the bottoms fraction 20.

The purified TAME, recovered as an overheads 22 from the heavies column, may then be superheated and vaporized via medium or high pressure steam 24 (heat exchanger not illustrated) then fed into a decomposition reactor 26, in which the decomposition reactions take place over an appropriate decomposition catalyst, converting the TAME to the constituent olefin and alcohol, isoamylene and methanol. As the TAME decomposition reaction is an endothermic reaction, medium or high pressure steam 24 is also used to provide the heat needed in the decomposition reactors.

The vapor phase decomposition reaction may be carried out at a temperature between about 130° C. to 260° C. and at a pressure of between about 2 barg to 12 barg. TAME then decomposes to 2-methyl-1-butene and 2-methyl-2-butene (IA). Any remaining TAA present in the reactor feed also decomposes to isoamylenes and water, at a similar decomposition rate depending on the age of the catalyst. The methanol produced from the decomposition reaction may also form dimethyl ether (DME) as a by-product. Other by-products formed in the reactor are DIA, isopentane and linear pentenes. Since the reactor condition is mild, the formation of DME and DIA are relatively low.

The decomposition reactor effluent 27 is then fed to a methanol recovery zone 28 to recover a methanol fraction 29, and an oxygenates and C5s fraction 30. Methanol recovery zone 28 may include various configurations to separate the methanol from the oxygenates and the target C5 olefins. In some embodiments, the decomposition reactor effluent 27 may initially be washed in a methanol extraction column (not shown) via countercurrent water washing to recover the methanol. The bottoms of the methanol extraction column, mainly methanol, water and some TAA, may then be sent to a methanol recovery column (MRC) (not shown) to recover methanol fraction 29.

The C5s and similar boiling components recovered via flow line 30 from the methanol recovery zone, including IA, linear pentenes, DME, DIA, and unconverted TAME, may then be sent to an Isoamylene Lights column 34 to vent 33 any DME formed from the rest of the methanol-free reactor effluent 38 that then feeds the Isoamylene Finishing Column 40.

Depending on the amount of TAA present in the MRC feed, a side draw may be taken from the tower 38 to purge out any TAA in some embodiments. The bottoms 38 of the Isoamylene Lights Column 34 is mostly C5s and oxygenates is then sent to an isoamylene finishing column 40, where the high purity isoamylene is taken overhead as product 42. The bottoms 44 from the isoamylene Finishing Column, including the unreacted TAME and TAA, is then recycled to the front end purification section 12 to optimize the production of isoamylene.

The recovered isoamylene fraction 42 may have an isoamylene content greater than 90 weight percent; greater than 95 weight percent in other embodiments; greater than 97 weight percent in other embodiments; greater than 98 weight percent in other embodiments; greater than 98.5 weight percent in other embodiments; greater than 99 weight percent in other embodiments; greater than 99.1 weight percent in other embodiments; and greater than 99.5 weight percent in yet other embodiments. In other embodiments, the isoamylene recovered may have a purity of at least 99.9 weight percent.

The methanol 29 recovered in methanol recovery zone 28 may then be sent to the upstream TAME unit to reduce the methanol requirement of the TAME unit. This stream effectively integrates TAME production and isoamylene production, providing desired synergies with respect to raw material consumption.

For a TAME decomposition unit fully integrated with a TAME unit, the Isoamylene Lights Column 34 may be located before the Methanol Recovery zone 28. In this configuration, the bottoms of the Isoamylene Lights Column 34 contains the unreacted oxygenates for recycle and the overhead stream then feeds the Methanol Extraction Column. The overhead of the methanol extraction column is the methanol-free C5s that eventually feeds Isoamylene Finishing Column 40 where DME is vented overhead. Bottom stream 44 in this case is the high purity isoamylene product.

Figure 2:
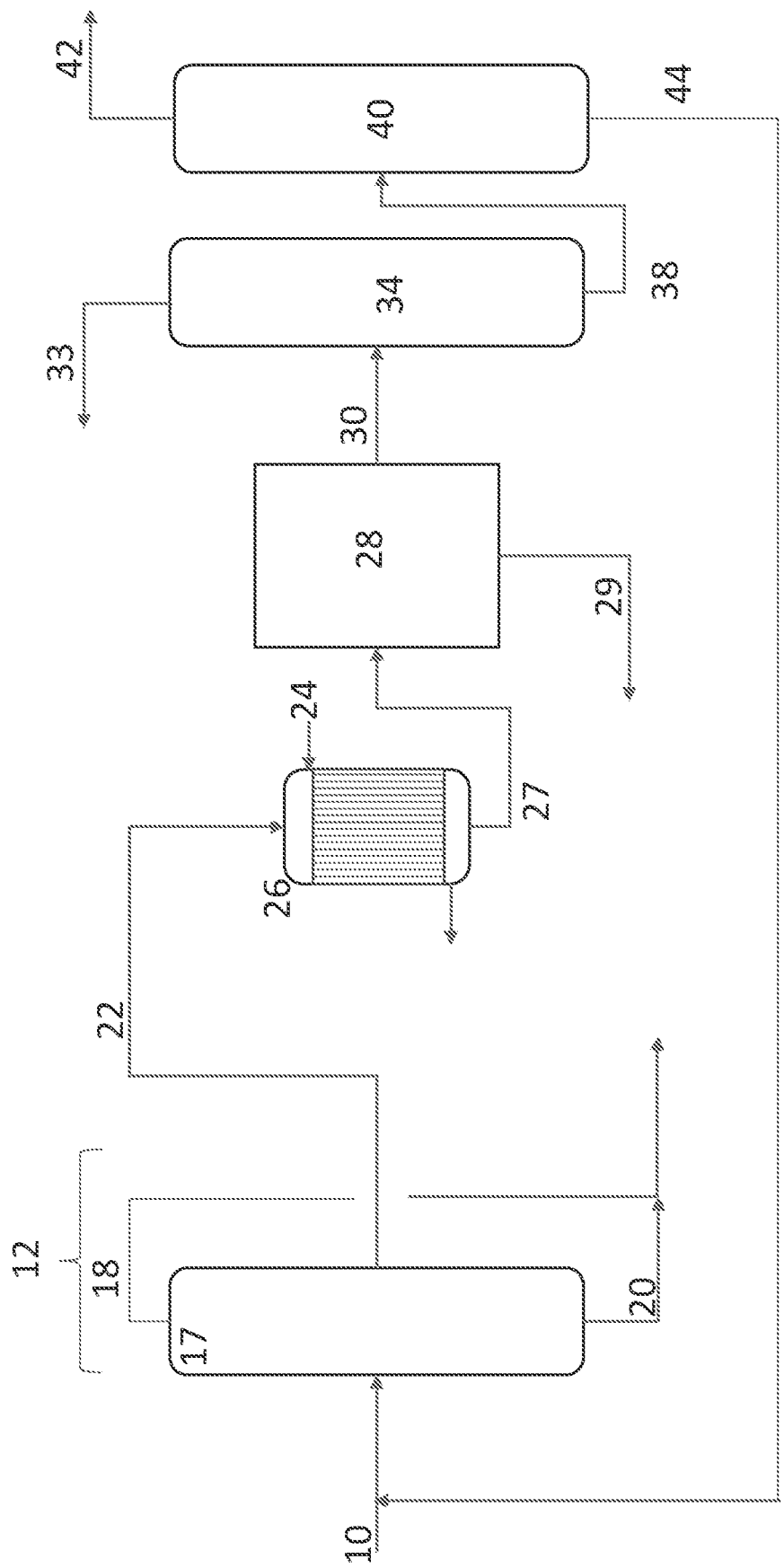
FIG. 2 illustrates a simplified process flow diagram for producing a high purity isoamylene according to one or more embodiments disclosed herein.

Referring now to FIG. 2, a simplified process flow diagram of a system for producing high purity isoamylene according to embodiments herein is illustrated, where like numerals represent like parts. In this embodiment, the separations conducted in the first two distillation columns (14, 16 of FIG. 1) are combined within a divided wall distillation column 17 to recover the purified TAME 22 as a side draw. The remaining components of the back-cracking process, separations, and recycle, are as described with respect to FIG. 1.

As described above, embodiments herein may produce a high purity isoamylene stream via TAME decomposition. Embodiments herein may thus be useful in expanding the use of TAME beyond gasoline blending uses, opening a new route for the use of TAME in petrochemical applications. Isoamylene present in steam cracker unit C5s or light cut naphtha, for example, is difficult to separate from linear pentenes through conventional distillation. Converting the isoamylene to TAME via etherification, followed by decomposition, as described herein, may advantageously result in a high purity isoamylene with very low impurities that is suitable for petrochemical applications in the production of fragrances, pesticides, peroxides, polymer antioxidant and hydrocarbon resin. Embodiments herein may thus be useful in expanding the purpose of gasoline blending TAME units while preserving use of much of the existing equipment in these units.

Unless defined otherwise, all technical and scientific terms used have the same meaning as commonly understood by one of ordinary skill in the art to which these systems, apparatuses, methods, processes and compositions belong. The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed as new and desired to be protected by Letters Patent is:

1. A system for producing a high purity isoamylene stream, the system comprising:
 a purification zone comprising a divided wall distillation column configured to receive a crude tertiary amyl ether from a feed source, the divided wall distillation column configured to separate the crude tertiary amyl ether into an overhead lights stream, a bottom heavies stream, and a tertiary amyl ether containing side draw stream;
a decomposition reactor containing a decomposition catalyst configured to convert the tertiary amyl ether as a vapor into isoamylene and alcohol and to produce a reaction effluent;
a separation zone configured to receive the reaction effluent and to separate the reaction effluent into an alcohol stream, a vent stream, a heavy oxygenate stream, and an isoamylene product stream.

2. The system of claim 1, further comprising a feed line for feeding the heavy oxygenate stream to the purification zone.

3. The system of claim 1, further comprising a reaction zone configured to react an isoamylene containing stream with methanol to produce the crude tertiary amyl ether.

4. The system of claim 3, wherein the separation zone comprises:
an isoamylene lights column configured to receive the reactor effluent and to separate the reactor effluent into an overhead stream and a bottoms stream comprising the heavy oxygenates, recovered as the heavy oxygenate stream;
a methanol extraction column, configured to receive the overhead stream from the isoamylene lights column and to recover an overheads stream and to recover the alcohol stream as a bottoms stream;
an isoamylene finishing column, configured to receive the overheads stream from the methanol extraction column and to recover the vent stream as an overheads product and to recover the isoamylene product stream as a bottoms product.

5. The system of claim 4, further comprising a flow line for feeding the alcohol stream to the reaction zone.

6. The system of claim 1, wherein the separation zone comprises:
a methanol extraction column, configured to receive the reactor effluent and to separate the reactor effluent into an overhead stream and a bottoms stream comprising the alcohol, recovered as the alcohol stream;
an isoamylene lights column configured to receive the overhead stream from the methanol extraction column and to recover the vent stream as an overheads and a bottoms stream;
a heavies column, configured to receive the bottoms stream from the isoamylene lights column and to recover the isoamylene product stream as an overheads product and to recover the heavy oxygenate stream as a bottoms product.

7. The system of claim 6, further comprising a methanol finishing column configured for receiving the alcohol stream and for producing a purified alcohol product stream.

8. The system of claim 1, further comprising a heat exchanger for vaporizing the tertiary amyl ether containing side draw stream.

9. The system of claim 8, further comprising a feed line for feeding the heavy oxygenate stream to the purification zone.

10. The system of claim 8, further comprising a reaction zone configured to react an isoamylene containing stream with methanol to produce the crude tertiary amyl ether.

11. The system of claim 10, wherein the separation zone comprises:
an isoamylene lights column configured to receive the reactor effluent and to separate the reactor effluent into an overhead stream and a bottoms stream comprising the heavy oxygenates, recovered as the heavy oxygenate stream;
a methanol extraction column, configured to receive the overhead stream from the isoamylene lights column and to recover an overheads stream and to recover the alcohol stream as a bottoms stream;
an isoamylene finishing column, configured to receive the overheads stream from the methanol extraction column and to recover the vent stream as an overheads product and to recover the isoamylene product stream as a bottoms product.

12. The system of claim 11, further comprising a flow line for feeding the alcohol stream to the reaction zone.

13. The system of claim 8, wherein the separation zone comprises:
a methanol extraction column, configured to receive the reactor effluent and to separate the reactor effluent into an overhead stream and a bottoms stream comprising the alcohol, recovered as the alcohol stream;
an isoamylene lights column configured to receive the overhead stream from the methanol extraction column and to recover the vent stream as an overheads and a bottoms stream;
a heavies column, configured to receive the bottoms stream from the isoamylene lights column and to recover the isoamylene product stream as an overheads product and to recover the heavy oxygenate stream as a bottoms product.

14. The system of claim 13, further comprising a methanol finishing column configured for receiving the alcohol stream and for producing a purified alcohol product stream.

15. A system for producing a high purity isoamylene stream, the system comprising:
a reaction zone configured to react an isoamylene containing stream with methanol to produce a crude tertiary amyl ether;
a purification zone comprising a divided wall distillation column configured to receive the crude tertiary amyl ether from a feed source, the divided wall distillation column configured to separate the crude tertiary amyl ether into an overhead lights stream, a bottom heavies stream, and a tertiary amyl ether containing side draw stream;
a heat exchanger for vaporizing the tertiary amyl ether containing side draw stream;
a decomposition reactor containing a decomposition catalyst configured to convert the tertiary amyl ether into isoamylene and alcohol and to produce a reaction effluent; and
a separation zone configured to receive the reaction effluent and to separate the reaction effluent into an alcohol stream, a vent stream, a heavy oxygenate stream, and an isoamylene product stream; and a feed line for feeding the heavy oxygenate stream to the purification zone,
wherein the separation zone comprises:
an isoamylene lights column configured to receive the reactor effluent and to separate the reactor effluent into an overhead stream and a bottoms stream comprising the heavy oxygenates, recovered as the heavy oxygenate stream;
a methanol extraction column, configured to receive the overhead stream from the isoamylene lights column and to recover an overheads stream and to recover the alcohol stream as a bottoms stream; and an isoamylene finishing column, configured to receive the overheads stream from the methanol extraction column and to recover the vent stream as an overheads product and to recover the isoamylene product stream as a bottoms product.

16. The system of claim 15, further comprising a flow line for feeding the alcohol stream to the reaction zone.

17. The system of claim 15, further comprising a methanol finishing column configured for receiving the alcohol stream and for producing a purified alcohol product stream.

* * * * *